United States Patent
Nadon et al.

(10) Patent No.: US 6,876,929 B2
(45) Date of Patent: *Apr. 5, 2005

(54) PROCESS FOR REMOVING SYSTEMATIC ERROR AND OUTLIER DATA AND FOR ESTIMATING RANDOM ERROR IN CHEMICAL AND BIOLOGICAL ASSAYS

(76) Inventors: Robert Nadon, 35 South Drive, St. Catharines, Ontraio (CA), L2R 4T9; Peide Shi, 44 Boneset Road, North York, Ontario (CA), M2J 4X4; Peter Ramm, 290 Riverview Boulevard, St. Catharines, Ontario (CA), L2T 3N4

( * ) Notice: Subject to any disclaimer, the term of this patent is extended or adjusted under 35 U.S.C. 154(b) by 136 days.

This patent is subject to a terminal disclaimer.

(21) Appl. No.: 10/021,734

(22) Filed: Nov. 8, 2001

(65) Prior Publication Data

US 2002/0094535 A1 Jul. 18, 2002

Related U.S. Application Data

(63) Continuation of application No. PCT/IB00/00810, filed on Jun. 19, 2000.
(60) Provisional application No. 60/155,173, filed on Sep. 21, 1999, and provisional application No. 60/139,639, filed on Jun. 17, 1999.

(51) Int. Cl.[7] .................... G06F 19/00; C12Q 1/68
(52) U.S. Cl. ................................ 702/19; 435/6
(58) Field of Search ................. 702/19; 435/6

(56) References Cited

U.S. PATENT DOCUMENTS 6,567,750 B1 * 5/2003 Nadon et al. ............... 702/19

* cited by examiner

*Primary Examiner*—John S. Brusca
(74) *Attorney, Agent, or Firm*—Darby & Darby

(57) ABSTRACT

A method for improving the reliability and/or accuracy of physical measurements obtained from array hybridization studies performed on an array having a large number of genomic samples uses a small number of replicates insufficient for making precise and valid statistical inferences. This is overcome by estimating an error in measurement of a sample by averaging errors obtained when measuring the large number of samples or a subset of the large number of samples. The estimated sample error is utilized as a standard for accepting or rejecting the measurement of the respective sample. The samples may be independent or dependent in that correlated across two or more conditions.

4 Claims, 2 Drawing Sheets

Fig. 1. Normalization method.
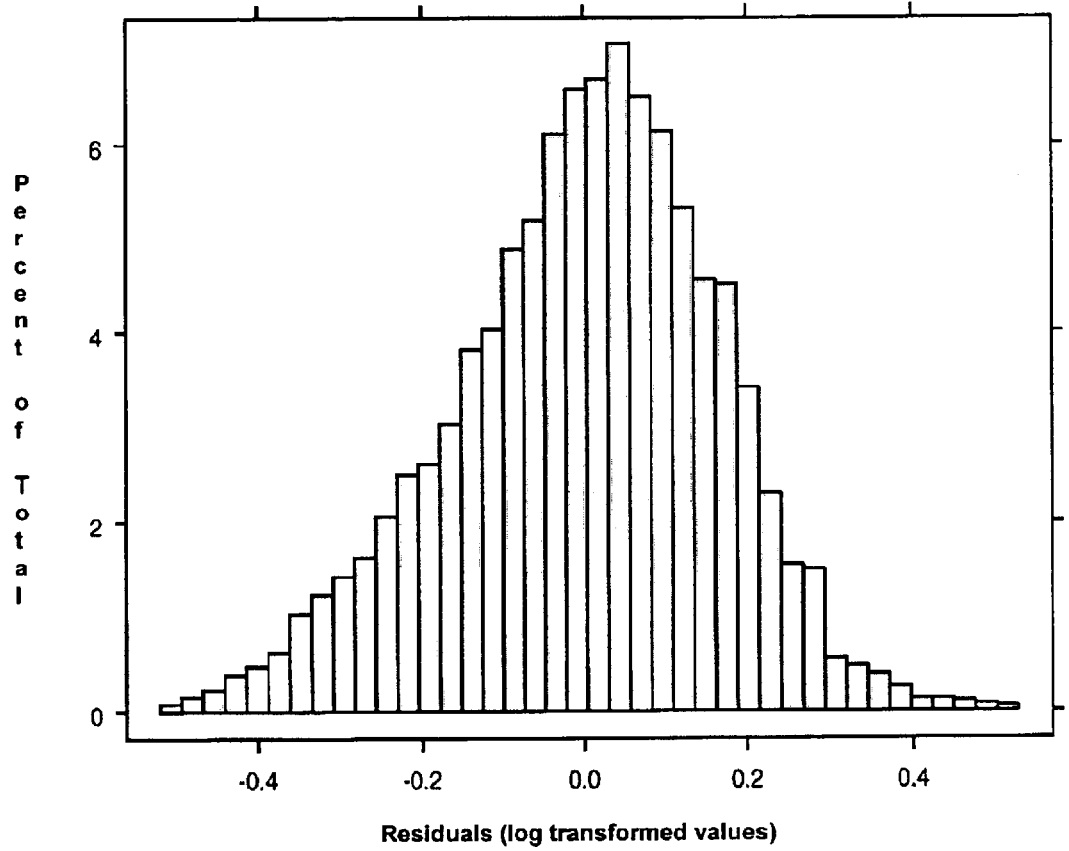

Fig. 2. Statistical modeling method.
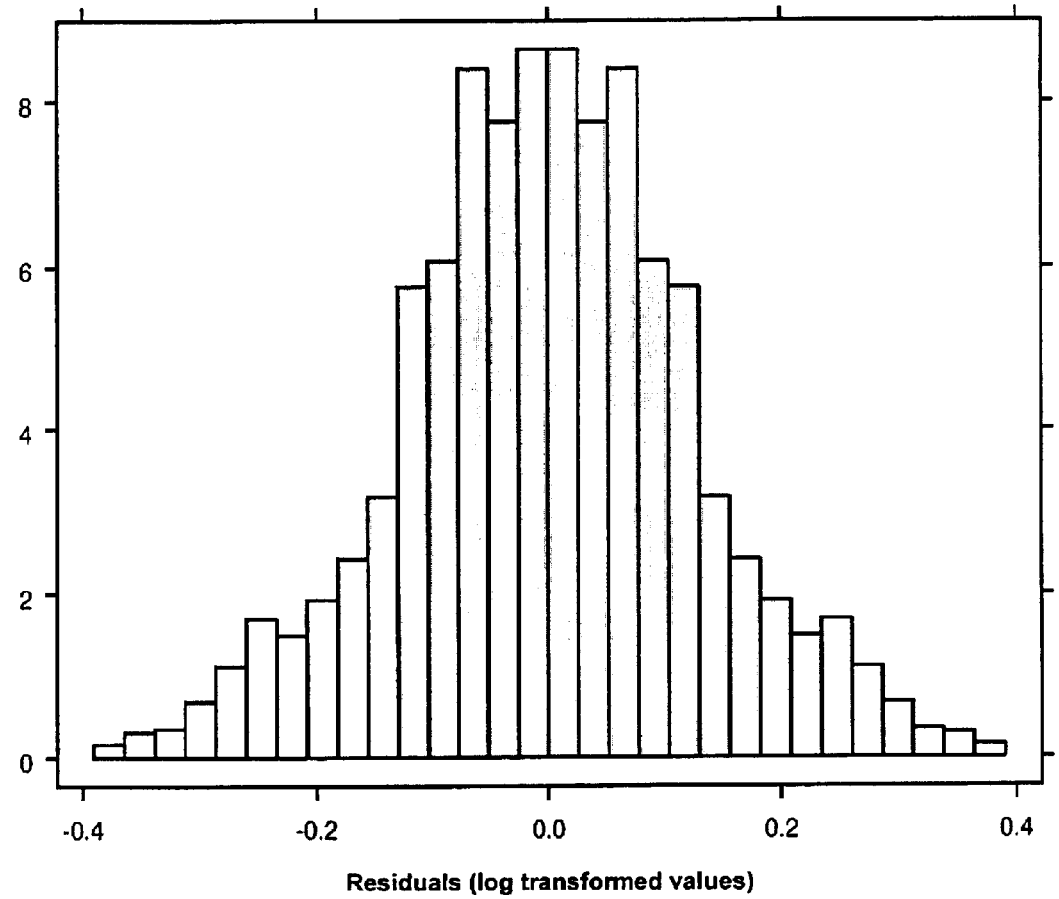
Residuals (log transformed values)

PROCESS FOR REMOVING SYSTEMATIC ERROR AND OUTLIER DATA AND FOR ESTIMATING RANDOM ERROR IN CHEMICAL AND BIOLOGICAL ASSAYS

This patent application claims the priority of the following U.S. Provisional Patent Applications: 60/139,639 filed Jun. 17, 1999; and 60/155,173 filed Sep. 21, 1999. This is a continuation of international application Ser. No. PCT/IB00/00810, filed Jun. 19, 2000.

FIELD OF THE INVENTION

The present invention relates to a process for making evaluations which objectify analyses of data obtained from hybridization arrays. The present invention in one aspect is a process for removing systematic error present in replicate genomic samples. A second aspect, is a process for detecting and deleting extreme value data points (outliers). A third aspect is an optimization process for detecting and removing extreme value data points (outliers). A fourth aspect, is a process for estimating the extent of random error present in replicate genomic samples composed of small numbers of data points.

BACKGROUND OF THE INVENTION

Array-based genetic analyses start with a large library of cDNAs or oligonucleotides (probes), immobilized on a substrate. The probes are hybridized with a single labeled sequence, or a labeled complex mixture derived from a tissue or cell line messenger RNA (target). As used herein, the term "probe" will therefore be understood to refer to material tethered to the array, and the term "target" will refer to material that is applied to the probes on the array, so that hybridization may occur.

The term "element" will refer to a spot on an array. Array elements reflect probe/target interactions. The term "background" will refer to area on the substrate outside of the elements.

The term "replicates" will refer to two or more measured values of the same probe/target interaction. Replicates may be independent (the measured values are independent) or dependent (the measured values are related, statistically correlated, or reaction paired). Replicates may be within arrays, across arrays, within experiments, across experiments, or any combination thereof.

Measured values of probe/target interactions are a function of their true values and of measurement error. The term "outlier" will refer to an extreme value in a distribution of values. Outlier data often result from uncorrectable measurement errors and are typically deleted from further statistical analysis.

There are two kinds of error, random and systematic, which affect the extent to which observed (measured) values deviate from their true values.

Random errors produce fluctuations in observed values of the same process or attribute. The extent and the distributional form of random errors can be detected by repeated measurements of the same process or attribute. Low random error corresponds to high precision.

Systematic errors produce shifts (offsets) in measured values. Measured values with systematic errors are said to be "biased". Systematic errors cannot be detected by repeated measurements of the same process or attribute because the bias affects the repeated measurements equally. Low systematic error corresponds to high accuracy. The terms "systematic error", "bias", and "offset" will be used interchangeably in the present document.

An invention for estimating random error present in replicate genomic samples composed of small numbers of data points has been described by Ramm and Nadon in "Process for Evaluating Chemical and Biological Assays", International Application No. PCT/IB99/00734. In a preferred embodiment, the process described therein assumed that, prior to conducting statistical tests, systematic error in the measurements had been removed and that outliers had been deleted.

In accordance with one aspect, the present invention is a process that estimates and removes systematic error from measured values. In another aspect, it is a process for optimizing outlier detection and deletion. A second aspect is a process for detecting and deleting outliers. A third aspect is a process for optimizing outlier detection and deletion automatically. A fourth aspect is a process for estimating the extent of random error present in replicate genomic samples composed of small numbers of data points.

There are two types of systematic error potentially present in hybridization arrays.

Array elements may be offset within arrays. Typically, this offset is additive. It can derive from various sources, including distortions in the nylon membrane substrate (Duggan, Bittner, Chen, Meltzer, & Trent "Expression profiling using cDNA microarrays", *Nature Genetics*, 21, 10–14 (1999).

If present, the offset is corrected by a procedure called "background correction", which involves subtracting from the array element the intensity of a background area outside of the element.

Areas used for calculation of background can be close to the array element (e.g., a circle lying around the element), or distant (a rectangle lying around the entire array). Because offset within an array tends to be specific to individual array elements (even with relatively uniform background), areas close to the element are generally preferred for background correction.

Alternatively, background estimates can be obtained from "blank" elements (i.e., elements without probe material). In this procedure, "background" is defined differently from the more typical method described in the previous paragraph. Theoretically, blank element intensities are affected by the same error factors that affect non-element background areas (e.g., washing procedures) and also by error factors which affect element quantification but which are extraneous to the biological signal of interest (e.g., dispensing errors).

The present invention does not address the issue of background correction. In a preferred embodiment, background correction, as necessary, has been applied prior to estimation of systematic error and outlier detection. In a non-preferred embodiment, the process may still be applied to arrays which have not been corrected for background offset.

In one aspect, the present invention is a process for estimating and removing systematic error across arrays. Contrary to background offset, offset across arrays tends to be proportional.

Offset across arrays can derive from various sources. For microarray studies which use fluorescent labelling, offset factors include target quantity, extent of target labelling, fluor excitation and emission efficiencies, and detector efficiency. These factors may influence all elements equally or may in part be specific to element subsets of the array. For example, quantity of target material may be offset differently for different robotic arrayer spotting pin locations (see Bowtell "Options available—from start to finish—for obtaining expression data by microarray" *Nature Genetics*, 21, 25–32, p. 31 (1999).

For radio-labelled macro array studies, proportional offset factors include target quantity and target accessibility (Perret, Ferran, Marinx, Liauzun, et al. in "Improved differential screening approach to analyse transcriptional variations in organized cDNA libraries" *Gene*, 208, 103–115 (1998)).

Time of day that arrays are processed (Lander "Array of hope" *Nature Genetics*, 21, 3–4 (1999)) and variations in chemical wash procedures across experiments (Shalon, Smith, & Brown "A DNA microarray system for analyzing complex DNA samples using two-color fluorescent probe hybridization" *Genome Research*, 6, 639–645 (1996)) have also been cited as offset factors.

Prior art methods for removing systematic error are called "normalization" procedures. These procedures involve dividing array element values by a reference value. This reference can be based on all probes or on a subset (e.g., "housekeeping genes" whose theoretical expression levels do not change across conditions). However obtained, the reference can be estimated by one of various summary values (e.g., mean or a specified percentile).

Once systematic error has been removed, any remaining measurement error is, in theory, random. Random error reflects the expected statistical variation in a measured value. A measured value may consist, for example, of a single value, a summary of values (mean, median), a difference between single or summary values, or a difference between differences. In order for two values to be considered significantly different from each other, their difference must exceed a threshold defined jointly by the measurement error associated with the difference and by a specified probability of concluding erroneously that the two values differ (Type I error rate). Statistical tests are conducted to determine if values differ significantly from each other.

All of prior art normalization procedures, however, estimate systematic error outside of the context of a statistical model. Because these informal procedures make implicit (and often incorrect) assumptions about the structure of the data (e.g., form and extent of both systematic and random error), they often fail to adequately eliminate measurement bias and can introduce additional bias due to the normalization procedure itself. In a different scientific context, Freedman and Navidi, in "Regression models for adjusting the 1980 census", *Statistical Science*, 1, 3–11 (1986) described the problems inherent in failing to correctly model data that contain measurement error ("uncertainty" in their terminology):

Models are often used to decide issues in situations marked by uncertainty. However, statistical inferences from data depend on assumptions about the processes which generated those data. If the assumptions do not hold, the inferences may not be reliable either. This limitation is often ignored by applied workers who fail to identify crucial assumptions or subject them to any kind of empirical testing. In such circumstances, using statistical procedures may only compound the uncertainty (p. 3).

In addition to correct removal of systematic error, many statistical tests require the assumption that residuals be normally distributed. Residuals reflect the difference between values' estimated true scores and their observed (measured) scores. If a residual score is extreme (relative to other scores in the distribution), it is called an outlier. An outlier is typically removed from further statistical analysis because it generally indicates that the measured value contains excessive measurement error that cannot be corrected. In order to achieve normally distributed residuals, data transformation is often necessary (e.g., log transform).

In one aspect, the present invention is a process for detecting and removing outliers by examining the distribution of residuals. In another aspect, it is a process for detecting and removing outliers automatically through an iterative process which examines characteristics of the distribution of residuals (e.g., skewness, kurtosis).

As with correction for offset across arrays (normalization), prior art for outlier detection relies on informal and arbitrary procedures outside of the context of a statistical model. For example, Perret, Ferran, Marinx, Liauzun, et al. "Improved differential screening approach to analyse transcriptional variations in organized CDNA libraries" *Gene*, 208, 103–115 (1998), compared the intensity of sets of two replicate array elements after normalization. Any replicate set that showed a greater than 2-fold difference (or equivalently, less than a 0.5-fold difference) was regarded as an outlier.

In accordance with one aspect, the present invention is a process for estimating the extent of random error present in replicate genomic samples composed of small numbers of data points and for conducting a statistical test comparing expression level across conditions (e.g., diseased versus normal tissue). It is an alternative to the method described by Ramm and Nadon in "Process for Evaluating Chemical and Biological Assays", International Application No. PCT/IB99/00734. As such, it can be used in addition to (or in place of) the procedures described by Ramm and Nadon (ibid).

Disadvantages of all prior art procedures include:
1. The value chosen as a normalization reference (e.g., $75^{th}$ percentile, etc.) is arbitrary;
2. Given that the choice of normalization reference is arbitrary, dividing by the reference value overcorrects some elements and undercorrects others;
3. Because prior art procedures do not estimate systematic error within the context of a statistical model, data transformations that are necessary for correct inferences may not be performed or may be applied incorrectly;
4. Because prior art procedures do not estimate systematic error within the context of a statistical model, normalization can alter the true structure of the data;
5. Because prior art procedures do not detect outliers within the context of a statistical model, true outliers may go undetected and non-outliers may be incorrectly classified as outliers;
6. Classification of values as outliers or not is arbitrary and subjective;
7. Theoretical assumptions about data structure (e.g., that residuals are normally distributed) are not examined empirically.
8. Normalization procedures may create additional measurement error that is not present in the original non-normalized measurements The term "treatment condition" will refer to an effect of interest. Such an effect may pre-exist (e.g., differences across different tissues or across time) or may be induced by an experimental manipulation.

Hybridization arrays produced under different treatment conditions may be statistically dependent or independent.

Microarray technology in which two different target treatment samples are labelled with different fluors and are then cohybridized onto each arrayed element represent one example of statistical dependence. Typically, expression ratios of the raw signals generated by the two fluors are examined for evidence of differences across treatment conditions.

Chen, Dougherty, & Bittner "Ratio-based decisions and the quantitative analysis of cDNA microarray images", *Journal of Biomedical Optics*, 2, 364–374 (1997) have presented an analytical mathematical approach that estimates the distribution of non-replicated differential ratios under the null hypothesis. This approach is similar to the present invention in that it derives a method for obtaining confidence intervals and probability estimates for differences in probe intensities across different conditions. It differs from the present invention in how it obtains these estimates. Unlike the present invention, the Chen et al. approach does not obtain measurement error estimates from replicate probe values. Instead, the measurement error associated with ratios of probe intensities between conditions is obtained via mathematical derivation of the null hypothesis distribution of ratios. That is, Chen et al. derive what the distribution of ratios would be if none of the probes showed differences in measured values across conditions that were greater than would be expected by "chance." Based on this derivation, they establish thresholds for statistically reliable ratios of probe intensities across two conditions. The method, as derived, is applicable to assessing differences across two conditions only. Moreover, it assumes that the measurement error associated with probe intensities is normally distributed. The method, as derived, cannot accommodate other measurement error models (e.g., lognormal). It also assumes that all measured values are unbiased and reliable estimates of the "true" probe intensity. That is, it is assumed that none of the probe intensities are "outlier" values that should be excluded from analysis. Indeed, outlier detection is not possible with the approach described by Chen et al.

The present invention applies the processes described by Ramm and Nadon in "Process for Evaluating Chemical and Biological Assays". International Application No. PCT/IB99/00734 and by Ramm, Nadon and Shi in "Process for Removing Systematic Error and Outlier Data and for Estimating Random Error in Chemical and Biological Assays". Provisional Application No. 60/139,639 (1999) to two or more statistically dependent genomic samples.

The present invention differs from prior art in that:

1. It can accommodate various measurement error models (e.g., lognormal);
2. It can detect outliers within the context of a statistical model;
3. It can be used to examine theoretical assumptions about data structure (e.g., that residuals are normally distributed).

DETAILED DESCRIPTION OF THE PREFERRED EMBODIMENT

Suppose, for example, that expression levels for a particular data set have proportional systematic and proportional random error across replicate arrays. This scenario is represented symbolically in Equation 1:

$$X_{gij} = \mu_{gi} v_{gj} \epsilon_{gij} \qquad (1)$$

For $g=1, \ldots, G$, $j=1, \ldots, m$ and $i=1, \ldots, n$, where $\mu_{gi}$ represents the associated true intensity value of array element i (which is unknown and fixed), $v_{gj}$ represents the unknown systematic shifts or offsets across replicates, and $\epsilon_{gij}$ represents the observed random errors in a given condition g for spot i and replicate j. The interest lies in obtaining an unbiased estimate of an element's "true" value ($\mu_{gi}$).

Given condition g (e.g., normal cells or diseased counterparts), array element i, and replicate j, the associated intensity value is denoted as $X_{gij}$.

Alternatively, a model with additive offset and additive random error would be symbolized by:

$$X_{gij} = u_{gi} + V_{gj} + e_{gij} \qquad (2)$$

For $g=1, \ldots, G$, $j=1, \ldots, m$ and $i=1, \ldots, n$, where $u_{gi}$ represents the associated true intensity value of array element i (which is unknown and fixed) $V_{gj}$ represents the unknown systematic shifts or offsets across replicates, and $e_{gij}$ represents the observed random errors in a given condition g for element i and replicate j. The interest lies in obtaining an unbiased estimate of an element's "true" value ($u_{gi}$).

The model shown in Equation 1 will be presented as a preferred embodiment. Applications of the process using the model shown in Equation 2, however, would be obvious to one skilled in the art. Applications using other models (e.g., proportional offset and additive random error) would also be obvious to one skilled in the art.

To make the parameters $v_{gj}$ ($V_{gj}$) identifiable in the model, the restriction that $\Sigma_{j=1}^{m} \log(v_{gj}) = 0$ ($\Sigma_{j=1}^{m} V_{gj} = 0$) is required.

These parameters can be taken to be fixed or random. When the parameters are assumed to be random, we assume further that they are independent of the random errors.

Under the model shown in Equation 1, for example, we have the maximum likelihood estimate (MLE) of $\mu_{gi}$ and $v_{gj}$ as follows:

$$\hat{\mu}_{gi} = \exp\left\{\frac{1}{m}\sum_{j=1}^{m} \log(X_{gij})\right\} \qquad (3)$$

and $$\hat{v}_{gj} = \exp\left\{\frac{1}{n}\sum_{i=1}^{n} \log(X_{gij}) - \log(\hat{\mu}_{gi}))\right\} \qquad (4)$$

Combining Equations 3 and 4 yields the estimate of the residuals [$\log(\hat{\epsilon}_{gij})$] shown in Equation 5.

$$\log(\hat{\epsilon}_{gij}) = \log(X_{gij}) - \log(\hat{\mu}_{gi}) - \log(\hat{v}_{gj}) \qquad (5)$$

Because for given g and i, $\log(X_{gij}) - \log(v_{gj}) = \log(\mu_{gi}) + \log(\epsilon_{gij})$, $j=1, \ldots, m$ are independent and identically distributed as normal distribution with mean $\log(\mu_{gi})$ and variance $\sigma^2_{gi}$, Equation 6 provides unbiased estimates of array elements' true values. That is, Equation 6 provides the estimated values with systematic error removed.

$$\log(X_{gij}) - \log(\hat{v}_{gj}) \qquad (6)$$

It is assumed that if the model is correct, the residuals should be normally distributed. This assumption can be assessed empirically by examining the skewness and the kurtosis of the distribution of the residuals as calculated according to Equation 5 (skewness and kurtosis measures are standard statistical indices; see Stuart & Ord "Distribution theory (6th ed.) (Kendall's advanced theory of statistics Vol. 1)", New York: Halsted Press (1994). Skewness is a measure of the symmetry of a distribution. Kurtosis is a measure of "peakedness" of a distribution. Under the normality assumption, both skewness and kurtosis of the residual distribution should be approximately zero.

Even if the model is correct for most of the data, outliers may cause the distribution of the entire data set to deviate from normality. Outliers can be detected and removed by one of the following optimization procedures:

1. Outliers may be defined by a threshold (e.g., ±2 standard errors away from the mean of the residuals). In a preferred embodiment, any residual whose absolute value exceeds the threshold would be deleted from further statistical tests.
2. An automatic iterative process that examines skewness and kurtosis may also be used. In this procedure, skewness and kurtosis are calculated for a middle proportion of scores (e.g., the middle 80%). Skewness and kurtosis are calculated repeatedly as the proportion of scores is increased in successive steps. The proportion of scores which produces optimal skewness and kurtosis values (i.e., closest to zero) is chosen as the optimal distribution of residuals. Scores which fall outside of the selected middle proportion of values are estimated as outliers. In a preferred embodiment, these scores are deleted from further analysis.

Statistical indices (e.g., confidence intervals) and statistical tests (e.g., t-tests, analyse-of-variance) as described by Ramm and Nadon in "Process for Evaluating Chemical and Biological Assays". International Application No. PCT/IB99/00734, can then be applied to the array element data whose residual scores are not outliers.

In addition or alternatively, the statistical test described in Equations 7 and 8 can be applied to the data.

$$z^* = \sqrt{m} \frac{(\overline{X}_{1i} - \overline{X}_{2i})}{\sqrt{\sigma_1^{2*} + \sigma_2^{2*}}} \quad (7)$$

Where $\sigma^{2*}$ for each condition is calculated as:

$$\sigma^{2*} = [\text{median}\{|x_i - \text{median}(x_i)|\}]^2 \cdot c^2 \quad (8)$$

Where $x_i$=all residuals for all replicated array elements within a condition and c is a normalizing factor for estimating the standard error of the residuals when they are normally distributed. Preferably, c=1.0532, but Other values of c may be substituted.

The $z^*$ value from Equation 7 is examined relative to a standard normal distribution (z-table) to assess level of statistical significance. Equations 7 and 8 generalize to three or more conditions in a manner that is obvious to one skilled in the art.

The present invention does not preclude the use of prior art normalization procedures being applied to the data before application of the present process. This may be necessary, for example, when data have been obtained across different conditions and different days. Under this circumstance, data within conditions may need to be normalized to a reference (e.g., housekeeping genes) prior to applying the present process.

Although preferred embodiments of the invention have been disclosed for illustrative purposes, those skilled in the art will appreciate that many additions, deletions and substitutions are possible, without departing from the scope or spirit of the invention as defined by the accompanying claims.

Appendix

Consider a case in which expression data were gathered from three replicate arrays that contained 1280 different elements. Systematic error across replicate arrays is assumed to be proportional and that random error across replicate arrays is also assumed to be proportional. This model is shown in Equation 1 in the main body of the text.

Normalization Method

One approach is to attempt to remove the proportional systematic error by dividing each element within an array by a reference value (e.g., $75^{th}$ percentile value of all elements within the array). If systematic error is removed by the normalization procedure, Equation 1 becomes:

$$x_{gij} = \mu_{gi} \epsilon_{gij}$$

Residuals are then calculated according to Equation 5 with the term for systematic error removed:

$$\log(\hat{\epsilon}_{gij}) = \log(X_{gij}) - \log(\hat{\mu}_{gi})$$

FIG. 1 presents the distribution of the residuals with skewness and kurtosis optimized (i.e., closest to zero) and outliers deleted. Of 1280 residuals, 40 were detected as outliers and deleted. The skewness and kurtosis values are −0.27, z=3.88; p<0.0001, and 0.0006, z=0.004, p=0.49, respectively. The skewness value departs significantly from zero, indicating that the residuals are not normally distributed. This result suggests that, contrary to the assumption of the model, normalization has not adequately removed the systematic error component from the measured expression values.

Present Invention Method

In one preferred embodiment, the present invention would proceed as follows:

1. Assume the measurement model shown in Equation 1.
2. Calculate the average of each element location across replicate arrays (Equation 3).
3. Estimate the systematic error for each array (Equation 4).
4. Calculate the residuals for each array element location (Equation 5).

FIG. 2 presents the distribution of the residuals with skewness and kurtosis optimized (i.e., closest to zero) and outliers deleted. Of 1280 residuals, 65 were detected as outliers and deleted. The skewness and kurtosis values are 0.073, z=1.04; p=0.15, and 0.039, z=0.28, p=0.39, respectively. The skewness and kurtosis values are not significantly different from zero, indicating that the residuals are approximately normally distributed. This result suggests that the statistical modeling process has adequately removed the systematic error component from the measured expression values.

Conclusion

In this example, the procedures described by Ramm and Nadon in "Process for Evaluating Chemical and Biological Assays". International Application No. PCT/IB99/00734 or the procedures of the present invention (Equations 7 and 8) would produce valid results with the "Present Invention Method" but not with the "Normalization Method". In other circumstances, depending on the measurement error model, prior art normalization procedures may be adequate for this purpose (e.g., proportional systematic error across arrays with additive random error). However, it is likely that the choice of the reference value for the normalization procedure will be arbitrary from a statistical inference perspective unless the processes are followed which are described in the present document and in Provisional Patent Application No. 60/082,692.

What is claimed is:

1. A method for improving the reliability of physical measurements obtained from array hybridization studies performed on an array having a first number of genomic samples, each composed of a number of replicates insufficient for making precise and valid statistical inferences, the number of replicates being less th the first number, comprising the step of estimating an error in measurement of a selected sample by averaging errors obtained when measuring at least one of the first number of samples and subset of the large number of samples, and utilizing the estimated sample error as a standard for accepting or rejecting the measurement of the selected sample.

2. The method of claim 1 wherein a physical measurement quantity is determined based on a difference between statistically dependent quantities.

3. The method of claim 1 wherein a physical measurement quantity determined from an entire array population is used to estimate discrete instances of that quantity for the number of replicate samples within that population.

4. The method of claim 1 wherein the estimates of measurement error are used to plan, manage and control array hybridization studies on the basis of (a) the probability of detecting a true difference of specified magnitude between physical measurements of a given number of replicates, or (b) the number of replicates required to detect a true difference of specified magnitude.

* * * * *